US006265416B1

(12) United States Patent
Bastian et al.

(10) Patent No.: US 6,265,416 B1
(45) Date of Patent: Jul. 24, 2001

(54) ANTITHROMBOTIC AGENTS

(75) Inventors: Jolie Anne Bastian, Beech Grove; Matthew Joseph Fisher, Mooresville; Richard Waltz Harper, Indianapolis; Ho-Shen Lin, Indianapolis; Jefferson Ray McCowan, Indianapolis; Daniel Jon Sall, Greenwood; Gerald Floyd Smith, Indianapolis; Kumiko Takeuchi, Indianapolis; Michael Robert Wiley, Indianapolis, all of IN (US); Minsheng Zhang, Warren, NJ (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/429,424

(22) Filed: Oct. 28, 1999

Related U.S. Application Data

(60) Provisional application No. 60/106,410, filed on Oct. 30, 1998.

(51) Int. Cl.[7] .................. A61K 31/535; A61K 31/44; C07D 413/00; C07D 471/02
(52) U.S. Cl. ................... 514/300; 514/234.5; 544/127; 546/113
(58) Field of Search ................. 514/234.5, 300; 544/127; 546/113

(56) References Cited

U.S. PATENT DOCUMENTS 5,684,014   11/1997   Müller et al. .................. 514/292

FOREIGN PATENT DOCUMENTS

| 0 668 279 | 8/1995 | (EP) . |
| 0 705 831 | 4/1996 | (EP) . |
| 0 802 183 | 10/1997 | (EP) . |
| WO 96/03375 | 2/1996 | (WO) . |
| WO 97/25033 | 7/1997 | (WO) . |
| WO 98/48797 | * 11/1998 | (WO) . |

OTHER PUBLICATIONS

D. Hands, et al., "A Convenient Method for the Preparation of 5–, 6– and 7–Azaindoles and Their Derivatives," *Journal of Synthetic Organic Chemistry*, pp. 877–882 (1996).
Robert M. Scarborough, "Chapter 8. Anticoagulant Strategies Targeting Thrombin and Factor Xa," *Annual Reports in Medicinal Chemistry*, (1995) 30, pp. 71–80.

* cited by examiner

*Primary Examiner*—Mukund J. Shah
*Assistant Examiner*—Ben Schroeder
(74) *Attorney, Agent, or Firm*—Arvie J. Anderson

(57) ABSTRACT

This application relates to novel compounds of formula I (and their pharmaceutically acceptable salts), as defined herein, processes and intermediates for their preparation, pharmaceutical formulations comprising the novel compounds of formula I, and the use of the compounds of formula I as thrombin inhibitors.

9 Claims, No Drawings

ANTITHROMBOTIC AGENTS

This application claims the benefit of U.S. Provisional Application No. 60/106,410, filed Oct. 30, 1998.

This invention relates to thrombin inhibitors which are useful anticoagulants in mammals. In particular it relates to 5- and 6-azaindole derivatives having high anticoagulant activity, and antithrombotic activity. Thus, this invention relates to new inhibitors of thrombin, pharmaceutical compositions containing the compounds as active ingredients, and the use of the compounds as anticoagulants for prophylaxis and treatment of pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Antithrombotic diamines are disclosed in International Patent Application Publication Number WO 97/25033.

Although the heparins and coumarins are effective anticoagulants, no commercial drug has yet emerged from the promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high oral bioavailability and favorable pharmacokinetics following oral administration.

According to the invention there is provided a compound of formula I (or a pharmaceutically acceptable salt thereof)

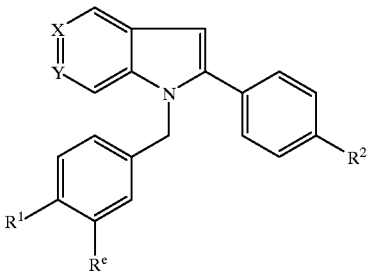

(I)

wherein
one of X and Y is N, and the other of X and Y is CH;
$R^e$ is hydrogen, methyl, methoxy or halo;
$R^1$ is carboxy, [(1–4C)alkoxy]carbonyl, hydroxymethyl, —CO—NR$^s$R$^t$ or —X$^1$—(CH$_2$)$_s$—NR$^s$R$^t$ in which X$^1$ is a direct bond, methylene or O; s is 1 or 2; provided that when s is 1, then X$^3$ is a direct bond; and R$^s$ and R$^t$ are independently hydrogen or (1–3C)alkyl or the group NR$^s$R$^t$ is pyrrolidino, piperidino, or morpholino; and
$R^2$ is —X$^2$—(CH$_2$)$_m$—NR$^a$R$^b$ in which X$^2$ is a direct bond, methylene, O or S; m is 1, 2, 3, 4 or 5; provided that when m is 1, then X$^2$ is a direct bond; and R$^a$ and R$^b$ are independently hydrogen or (1–3C)alkyl or the group NR$^a$R$^b$ is pyrrolidino, piperidino, or morpholino; or
$R^2$ is —X$^2$—(CH$_2$)$_n$—R$^f$ in which X$^2$ is a direct bond, methylene or O; n is 1, 2 or 3; and R$^f$ is 5-tetrazolyl, carboxy, [(1–4C)alkoxy]carbonyl or hydroxymethyl; and
provided that at least one of R$^1$ and R$^2$ includes a basic amino moiety —NR$^s$R$^t$ or —NR$^a$R$^b$.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) may exist in, and be isolated in, isomeric forms, including cis- or trans-isomers, as well as optically active, racemic, or diastereomeric forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of formula I (or salt of prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

A particular value for a (1–3C)alkyl group is, for example, methyl, ethyl, propyl or isopropyl, and for a (1–4C)alkoxy group is, for example, methoxy, ethoxy, isopropoxy or t-butoxy.

A particular value, independently, for $R^e$ is methyl, methoxy or bromo; for $R^1$ is —CO—$NR^sR^t$ or —$X^1$—$(CH_2)_s$—$NR^sR^t$; and for $R^2$ is —$X^2$—$(CH_2)_m$—$NR^aR^b$ or is —$X^2$—$(CH_2)_n$—$R^f$ in which $X^2$ is O; n is 3; and $R^f$ is carboxy, [(1–4C)alkoxy]carbonyl or hydroxymethyl.

A more particular value, independently, for $R^e$ is methoxy; for $R^1$ is pyrrolidinocarbonyl or pyrrolidinomethyl; and for $R^2$ is 2-pyrrolidinoethoxy.

A particular compound of formula I is one in which $R^e$ is methoxy and $R^1$ is pyrrolidinomethyl.

Specific compounds of formula I are described in the accompanying Examples.

A pharmaceutically acceptable salt of an antithrombotic agent of the instant invention includes one which is an acid-addition salt made with an acid which provides a pharmaceutically acceptable anion. Thus, an acid addition salt of a novel compound of formula I as provided above made with an acid which affords a pharmaceutically acceptable anion provides a particular aspect of the invention. Examples of such acids are provided hereinbelow. In addition, a compound of formula I which contains an acidic moiety forms a salt made with a base which provides a pharmaceutically acceptable anion.

As an additional aspect of the invention there is provided a pharmaceutical formulation comprising in association with a pharmaceutically acceptable carrier, diluent or excipient, a compound of formula I (or a pharmaceutically acceptable salt thereof) as provided in any of the above descriptions.

A compound of formula I may be made by processes which include processes known in the chemical art for the production of compounds structurally related to a compound of formula I or by a novel process described herein. A process for a compound of formula I (or a pharmaceutically acceptable salt thereof), novel processes for a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

In general, a compound of formula I may be prepared according to one of the routes outlined in Scheme I, and which are described in the examples, in which each of $Q^1$, $Q^2$ and $Q^e$, respectively, represents a value defined for the groups $R^1$, $R^2$ and $R^e$, a protected version of such a group, or moiety which can be further elaborated into such a group. Conveniently, the species of formula (A) is deprotonated using a strong base, and the resulting dianion is condensed with a benzamide, such as the Weinreb amide shown, and cyclized to afford an azaindole of formula (B). The 1-substituted azaindole of formula (C) is obtained by alkylating the azaindole of formula (B) with a reagent of formula (D). Final conversion of a group $Q^1$, $Q^2$ or $Q^e$ into $R^1$, $R^2$ or $R^e$ is carried out at a convenient point, consistent with the chemistry employed.

Scheme I

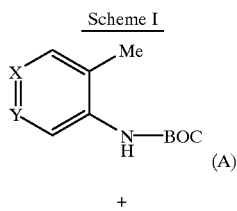

(A)

+

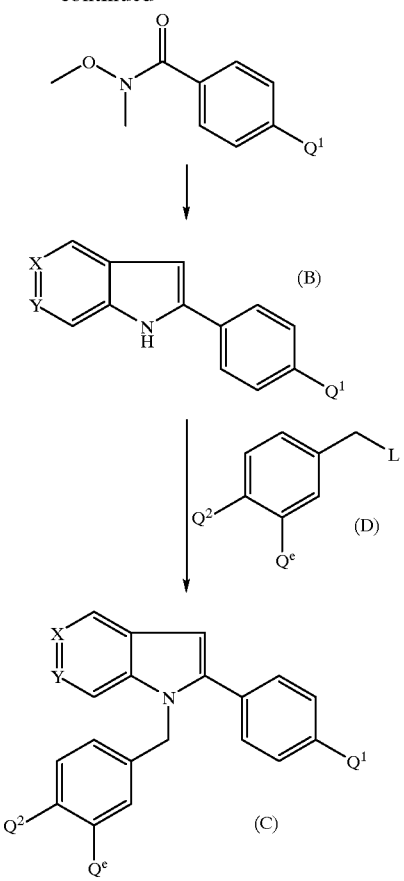

Thus, there is provided a process for preparing a compound of formula I (or a pharmaceutically acceptable salt thereof) as provided in any of the above descriptions which is selected from:

(a) Alkylating the 1-position of an azaindole of formula II

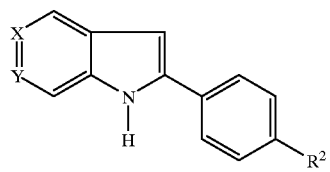

II using a compound of formula III

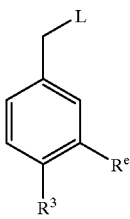

III wherein L is a conventional leaving group, for example using a procedure such as that described in Example 1-D;

(b) for a compound of formula I in which $R^1$ is —CO—$NR^sR^t$, amidating an ester of formula I in which $R^1$ is

[(1–4C)alkoxy]carbonyl (for example as described in Example 1-E) or an acid of formula I in which $R^1$ is carboxy or an activated derivative thereof with an amine of formula H—$NR^sR^t$; or (c) for a compound of formula I in which $R^1$ is —$CH_2$—$NR^sR^t$, reducing the carbonyl of a compound of formula I in which $R^1$ is —CO—$NR^sR^t$ (for example using a procedure such as that described in Example 2);

whereafter, for any of the above procedures, when a functional group is protected using a protecting group, removing the protecting group; and whereafter, for any of the above procedures, when a pharmaceutically acceptable salt of a compound of formula I is required, it is obtained by reacting the basic form of such a compound of formula I with an acid affording a physiologically acceptable counterion, or, for a compound of formula I which bears an acidic moiety, reacting the acidic form of such a compound of formula I with a base which affords a pharmaceutically acceptable cation, or by any other conventional procedure;

and wherein, unless otherwise described, X, Y, $R^1$, $R^2$ and $R^e$ have the values described above.

As used herein, a leaving group is a moiety which is displaced in a nucleophilic substitution reaction, for example a halo group (such as chloro, bromo or iodo), a sulfonate ester group (such as methylsulfonyloxy, p-toluylsulfonyloxy or trifluoromethylsulfonyloxy), or the reactive species derived from treating an alcohol with triphenylphospine, diethyl azodicarboxylate and triethyl amine (in a Mitsunobu reaction). An activated derivative of a carboxylic acid includes, for example, an ester (such as a methyl ester), an acid halide (such as an acid chloride), an activated ester (such as with 1-hydroxy-7-azabenzotriazole 1-hydroxybenzotriazole or N-hydroxysuccinimide), an anhydride with a carboxylic acid (such as by formed by reaction with butyl chloroformate) or an activated derivative formed by reaction with a coupling reagent (such as with a carbodiimide, for example with dicyclohexylcarbodiimide or with 1-(3-dimethyaminopropyl)-3-ethylcarbodiimide).

Novel intermediate or starting material compounds, such as an azaindole of formula II, provide further aspects of the invention.

As mentioned above, the invention includes pharmaceutically acceptable salts of the thrombin inhibiting compounds defined by the above formula I. A compound of formula I which bears an acidic moiety forms salts with pharmaceutically acceptable bases. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine. The potassium and sodium salt forms are particularly preferred.

A particular compound of formula I which possesses one or more sufficiently basic functional groups to react with any of a number of inorganic and organic acids affording a physiologically acceptable counterion forms a pharmaceutically acceptable acid addition salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

If not commercially available, the necessary starting materials for the preparation of a compound of formula I may be prepared by procedures which are selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Generally, the compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention provides a method of inhibiting thrombin comprising using an effective amount of a compound of formula I (or a pharmaceutically acceptable salt thereof) as provided in any of the descriptions herein.

The invention in one of its aspects provides a method of inhibiting thrombin in a mammal comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a novel compound of formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

|  |  |
| --- | --- |
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

|  |  |
| --- | --- |
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

|  |  |
| --- | --- |
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 ml dose, are made as follows:

|  |  |
| --- | --- |
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

The ability of the compounds of the present invention to be an effective and orally active thrombin inhibitor are evaluated in one or more of the following assays.

The compounds provided by the invention (formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 $\mu$L buffer (0.03 M Tris, 0.15 M NaCl, pH 7.4) with 25 $\mu$L of human thrombin solution (purified human thrombin, Enzyme Research Laboratories, South Bend, Ind., at 8 NIH units/mL) and 25 $\mu$L of test compound in a solvent (50% aqueous methanol (v:v)). Then 150 $\mu$L of an aqueous solution of the chromogenic substate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

$$\text{Thrombin} + I \rightleftharpoons \text{Thrombin} - \text{Kass} = \frac{[\text{Thrombin} - I]}{[(\text{Thrombin}) \times (I)]}$$

Kass is calculated for a range of concentrations of test compounds and the mean value reported in units of liter per mole. In general, a thrombin inhibiting compound of formula I of the instant invention exhibits a Kass of $0.1 \times 10^6$ L/mole or much greater.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/ plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 $\mu$L thrombin (73 NIH unit/mL) to 100 $\mu$L human plasma which contains 0.0229 µCi 125-iodine labeled fibrinogen. Clot lysis is studied by overlaying the clots with 50 µL of urokinase or streptokinase (50, 100, or 1000 unit/mL) and incubating for 20 hours at room temperature. After incubation the tubes are centrifuged in a Beckman Microfuge. 25 µL of supernate is added into 1.0 mL volume of 0.03 M tris/0.15 M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 µg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982). In this model preferred compounds of the instant invention reduce the net clot weight to approximately 25–30% of control, or even lower, at an i.v. dose of 33.176 µmol/kg/h.

$FeCl_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 µL is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269, 1990).

Spontaneous thrombolysis model

In vitro data suggests that thrombin inhibitors inhibit thrombin and, at higher concentrations, may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}I$ human Fibrogen (5 µCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, *Cardiovas. Pharmacol.*, 12:520, 1988).

Coagulation parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.1 mL, 0.025 M) is added to start coagulation. Assays are done in duplicate and averaged.

Index of Bioavailability

For a measure of bioactivity, plasma thrombin time (TT) serves as a substitute for the assay of parent compound on the assumption that observed increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{\text{AUC po}}{\text{AUC iv}} \times \frac{\text{Dose iv}}{\text{Dose po}} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/−SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment) Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hours after administration of test compound. Reocclusion of coronary arteries after successful thrombolysis is defined as zero CBF which persisted for at least 30 minutes.

Hematology and template bleeding time determinations

Whole blood cell counts, hemoglobin, and hematocrit values are determined on a 40-$\mu$L sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make two horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment. All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of p<0.05. All values are mean ± SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
AIBN=azobisisobutyronitrile
Anal.=elemental analysis
Bn or Bzl=benzyl
Bu=butyl
n-BuLi=butyllithium
Calcd=calculated
DCC=dicyclohexylcarbodiimide
DIBAL-H=diisobutyl aluminum hydride
DMF=dimethylformamide
DMSO=dimethylsulfoxide
Et=ethyl
EtOAc=ethyl acetate
Et$_3$N=triethylamine
Et$_2$O=diethyl ether
EtOH=ethanol
EtSH=ethanethiol
FAB=Fast Atom Bombardment (Mass Spectroscopy)
FDMS=field desorption mass spectrum
Hex=hexanes
HOAt=1-hydroxy-7-azabenzotriazole
HPLC=High Performance Liquid Chromatography
HRMS=high resolution mass spectrum
i-PrOH=isopropanol
IR=Infrared Spectrum
LAH=lithium aluminum hydride
Me=methyl
MeI=methyl iodide
MeOH=methanol
MPLC=Medium Pressure Liquid Chromatography
NBS=N-bromosuccinimide
NMR=Nuclear Magnetic Resonance
Ph=phenyl
i-Pr=isopropyl
Rochelle's Salt=potassium sodium tartrate
RPHPLC=Reversed Phase High Performance Liquid Chromatography
SiO$_2$ =silica gel
TBS=tert-butyldimethylsilyl
TFA=trifluoroacetic acid
THF=tetrahydrofuran
TIPS=triisopropylsilyl
TLC=thin layer chromatography
triflic acid=trifluoromethanesulfonic acid Unless otherwise stated, pH adjustments and work up are with aqueous acid or base solutions. PrepLC indicates preparative liquid chromatography using "Prep Pak (TM)" silica cartridges; radial chromatography indicates preparative chromatography using a "Chromatotron (TM)" instrument.

EXAMPLE 1

Preparation of 1-[2-Methoxy-4-(1-pyrrolidinylcarbonyl)-benzyl]-2-[4-[2-(1-pyrrolidinyl)ethoxy]phenyl]-5-azaindole Oxalate.

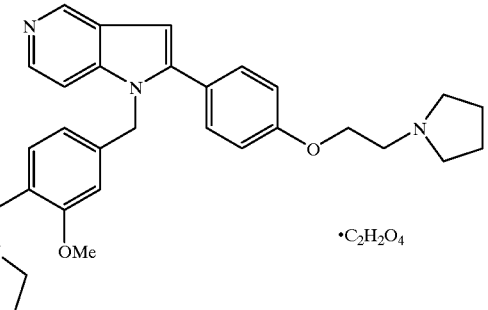

A. N-Methoxy-N-methyl-4-[2-(1-pyrrolidinyl)ethoxy]-benzamide.

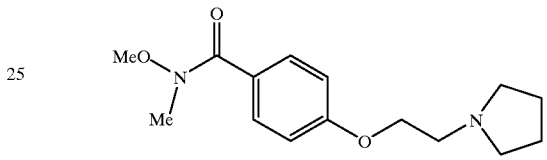

A slurry of 4-[2-(1-pyrrolidinyl)ethoxy]benzoic acid hydrochloride (30.0 g, 110.4 mmol) in 500 mL of dichloroethane was treated with 2 drops of DMF and (COCl)$_2$ (48 mL, 552 mmol). After 2 days at ambient temperature, the acid had completely dissolved. The reaction mixture was concentrated in vacuo, resuspended in dichloroethane and concentrated once again. The acid chloride was immediately dissolved in 500 mL dichloroethane and cooled to −10° C. The resulting solution was treated with N,O-dimethyl-hydroxylamine hydrochloride (11.8 g, 121.4 mmol). The resulting mixture was allowed to warm to room temperature. After stirring overnight, the reaction mixture was poured into 500 mL of saturated aqueous NaHCO$_3$. The layers were separated, and the aqueous layer was extracted with CHCl$_3$ (2×250 mL). The combined organic layers were dried over K$_2$CO$_3$, filtered and concentrated in vacuo. Purification of the crude residue by flash chromatography (SiO$_2$; gradient of 80:15:5 to 70:25:5 hexanes/THF/TEA) afforded 16.1 g (57.8 mmol, 52%) of the title Weinreb amide as a pale orange oil.

ISMS 279 (M+1);
Anal. for C$_{15}$H$_{22}$N$_2$O$_3$·0.5H$_2$O:
Calcd: C, 62.70; H, 8.07; N, 9.75;
Found: C, 62.63; H, 7.68; N, 9.55.

B. 2-[4-[2-(1-Pyrrolidinyl)ethoxy]phenyl]-5-azaindole.

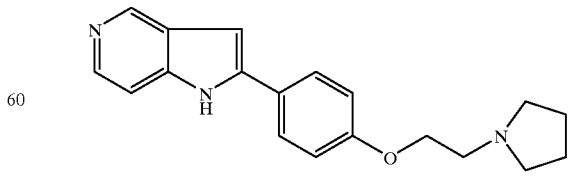

The title compound was prepared in 35% overall yield from the dianion of 4-t-butoxycarbonylamino-3-methylpyridine and N-methoxy-N-methyl-4-[2-(1- pyrrolidinyl)ethoxy]benzamide in a fashion similar to that described in *Synthesis* 1996, 877–882.

ISMS 308 (M+1), 306 (M−1);

Anal. for $C_{19}H_{21}N_3O$:

Calcd: C, 74.24; H, 6.89; N, 13.67;

Found: C, 74.54; H, 6.87; N, 13.70.

C. Methyl 4-Bromomethyl-2-methoxybenzoate.

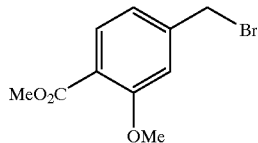

A mixture of 4-methylsalicylic acid (20 g, 131.5 mmol), $CH_3I$ (74.7 g, 526.3 mmol), and $K_2CO_3$ (36.2 g, 262 mmol) in 250 mL of acetone was maintained at reflux for 4 days. After filtering, the filtrate was concentrated under reduced pressure and the resulting residue taken up in $Et_2O$ and washed with 2 N NaOH. The organic extract was concentrated under reduced pressure. From this crude material, 10 g (55.6 mmol) was taken up in 100 mL of $CCl_4$; and N-bromo-succinimide (10.8 g, 61.1 mmol) and a catalytic amount of AIBN were added. The mixture was heated at reflux for 4 h and then diluted 10 fold with $Et_2O$. The organics were washed with 25% NaOH (aq.) and concentrated under reduced pressure. Crude product was recrystallized from EtOAc-hexanes, giving 14.2 g (99%) of the desired bromide.

$^1$H NMR (CDCl$_3$) δ 7.77 (d, J=8.3 Hz, 1H), 7.01 (d, J=2.6 Hz, 1H), 6.99 (s, 1H), 4.47 (s, 2H), 3.94 (s, 3H), 3.91(s, 3H).

D. Methyl 2-Methoxy-4-[[2- [4-[2-(1-pyrrolidinyl)ethoxy]-phenyl]-5-azaindol-1-yl]methyl]benzoate.

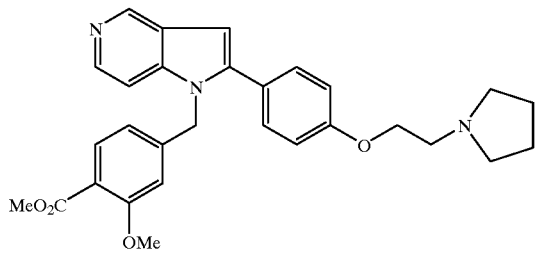

Powdered KOH (730 mg, 13.0 mmol) was added to 25 mL of DMSO at ambient temperature. After 10 min, 2-[4-[2-(1-pyrrolidinyl)ethoxy]phenyl]-5-azaindole (2.0 g, 6.5 mmol) was added. After 45 min, a solution of methyl 4-bromo-methyl-2-methoxybenzoate (1.69 g, 6.5 mmol) in 10 mL of DMSO was added dropwise via cannula. The resulting mixture was stirred overnight then poured into 100 mL of $H_2O$. The aqueous solution was extracted with EtOAc (3×100 mL). The combined organic layers were dried over $K_2CO_3$, filtered and concentrated in vacuo. Purification of the crude residue by radial chromatography (SiO$_2$; gradient of 0–2% MeOH/CHCl$_3$, saturated with NH$_4$OH) afforded 550 mg (1.13 mmol, 17%) of the title compound.

ISMS 486 (M+1); FAB HRMS: m/e, calcd for $C_{29}H_{32}N_3O_4$:

486.2393; Found: 486.2390 (M+1);

Anal. for $C_{29}H_{31}N_3O_4$:

Calcd: C, 71.73; H, 6.44; N, 8.65;

Found: C, 72.33; H, 6.92; N, 8.11.

E. 1-[2-Methoxy-4-(1-pyrrolidinylcarbonyl)benzyl]-2-[4-[2-(1-pyrrolidinyl)ethoxy]phenyl]-5-azaindole Oxalate.

A solution of methyl 2-methoxy-4-[[2-[4-[2-(1-pyrrolidinyl)ethoxy]phenyl]-5-azaindol-1-yl]methyl]benzoate (500 mg, 1.03 mmol) in 5 mL of pyrrolidine was heated at 120° C. in a sealed tube for 2 days. The reaction mixture was cooled to ambient temperature, diluted with CHCl$_3$ and concentrated in vacuo. Purification of the crude residue by radial chromatography (SiO$_2$; gradient of 1–3% MeOH/CHCl$_3$, saturated with NH$_4$OH) afforded 125 mg (0.238 mmol, 23%) of the free base.

A portion of the free base dissolved in a small amount of EtOAc was treated with a slight excess of oxalic acid in EtOAc. The resulting white precipitate was filtered and dried in vacuo to give the title oxalate salt as a white powder.

ISMS 525 (M+1);

Anal. for $C_{32}H_{36}N_4O_3 \cdot 1.85 C_2H_2O_4$:

Calcd: C, 62.03; H, 5.79; N, 8.11;

Found: C, 61.97; H, 6.03; N, 8.18.

EXAMPLE 2

Preparation of 1-[3-Methoxy-4-(1-pyrrolidinyl)methyl]benzyl-2-[4- [2-(1-pyrrolidinyl)ethoxy]phenyl]-5-azaindole Dioxalate.

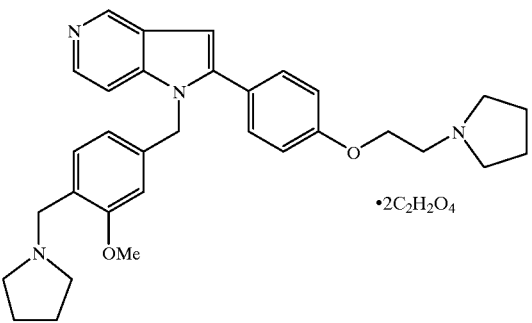

A 0° C. solution of 1-[2-methoxy-4-(1-pyrrolidinylcarbonyl)benzyl]-2-[4-[2-(1-pyrrolidinyl)ethoxy]phenyl]-5-azaindole (50 mg, 0.10 mmol) in 1 mL of THF was treated with LAH (0.285 mL, 0.286 mmol; 1 M in THF) dropwise. After 2 days at ambient temperature, the reaction mixture was quenched with 5 mL of cold $H_2O$. After CHCl$_3$ and saturated aqueous Rochelle's salt (20 mL each) were added, the layers were separated, and the aqueous layer was extracted with CHCl$_3$ (2×20 mL). The combined organic layers were dried over $K_2CO_3$, filtered and concentrated in vacuo. Purification of the crude residue by radial chromatography (SiO$_2$; gradient of 1–3% MeOH/CHCl$_3$, saturated with NH$_4$OH) afforded 30 mg (0.059 mmol, 62%) of the title compound, which was converted to its dioxalate salt by a method similar to that described in Example 1, Part E.

IR (KBr) 3421 (br), 1612 cm$^{-1}$;

ISMS 511 (M+1);

Anal. for $C_{32}H_{38}N_4O_2 \cdot 2.1 C_2H_2O_4 \cdot 1.3 H_2O$:

Calcd: C, 60.12; H, 6.24; N, 7.75;

Found: C, 60.29; H, 5.93; N, 7.35.

EXAMPLE 3

Preparation of 1-[2-Methoxy-4-(1-pyrrolidinylcarbonyl)-benzyl]-2-[4-[2-(1-pyrrolidinyl)ethoxy]phenyl]-6-azaindole Oxalate.

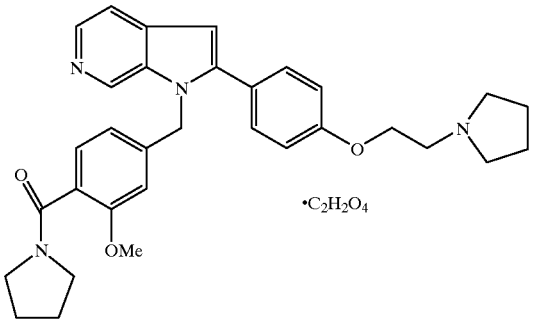

A. 2-[4-[2-(1-Pyrrolidinyl)ethoxy]phenyl]-6-azaindole.

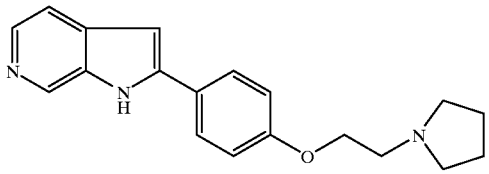

The title compound was prepared in 36% overall yield from the dianion of 3-t-butoxycarbonylamino-4-methylpyridine and N-methoxy-N-methyl-4-[2-(1-pyrrolidinyl)ethoxy]benzamide in a fashion similar to that described in Synthesis 1996, 877–882.

ISMS 308 (M+1), 306 (M-1);
Anal. for $C_{19}H_{21}N_3O \cdot 0.5H_2O$:
Calcd: C, 72.12; H, 7.01; N, 13.28;
Found: C, 72.20; H, 6.63; N, 13.05.

B. Methyl 2-Methoxy-4-[[2-[4-[2-(1-pyrrolidinyl)ethoxy]-phenyl]-6-azaindol-1-yl]methyl]benzoate.

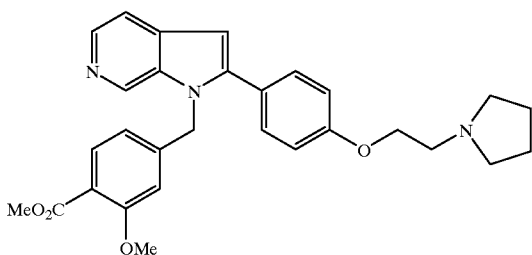

The title compound was prepared in 7% yield from 2-[4-[2-(1-pyrrolidinyl)ethoxy]phenyl]-6-azaindole and methyl 4-bromomethyl-2-methoxybenzoate by the procedure detailed in Example 1, Part D.

IR (KBr) 1722, 1611, 1247 cm$^{-1}$;
ISMS 486 (M+1); FAB HRMS: m/e, calcd for $C_{29}H_{32}N_3O_4$:
486.2393. Found: 486.2400 (M+1);
Anal. for $C_{29}H_{31}N_3O_4$:
Calcd: C, 71.73; H, 6.44; N, 8.65;
Found: C, 70.82; H, 6.23; N, 8.03.

C. 1-[2-Methoxy-4-(1-pyrrolidinylcarbonyl)benzyl]-2-[4-[2-(1-pyrrolidinyl)ethoxy]phenyl]-6-azaindole Oxalate.

The title compound was prepared in 16% yield from methyl 2-methoxy-4-[[2-[4-[2-(1-pyrrolidinyl)ethoxy]phenyl]-6-azaindol-1-yl]methyl]benzoate by the method described in Example 1, Part E.

IR (KBr) 3430 (br), 1632, 1610, 1476 cm$^{-1}$;
ISMS 525 (M+1);
Anal. for $C_{32}H_{36}N_4O_3 \cdot 1.9C_2H_2O_4$:
Calcd: C, 61.80; H, 5.77; N, 8.05;
Found: C, 61.86; H, 5.68; N, 8.25.

What is claimed is:

1. A compound of formula I (or a pharmaceutically acceptable salt thereof)

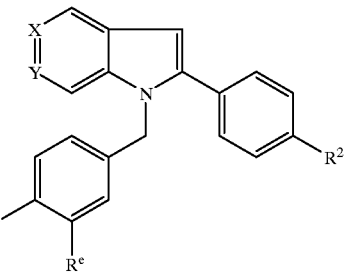

wherein
one of X and Y is N, and the other of X and Y is CH;
$R^e$ is hydrogen, methyl, methoxy or halo;
$R^1$ is carboxy, [(1–4C)alkoxy]carbonyl, hydroxymethyl, —CO—NR$^s$R$^t$ or —X$^1$—(CH$_2$)$_s$—NR$^s$R$^t$ in which X$^1$ is a direct bond, methylene or O; s is 1 or 2; provided that when s is 1, then X$^3$ is a direct bond; and R$^s$ and R$^t$ are independently hydrogen or (1–3C)alkyl or the group NR$^s$R$^t$ is pyrrolidino, piperidino, or morpholino; and $R^2$ is —X$^2$—(CH$_2$)$_m$—NR$^a$R$^b$ in which X$^2$ is a direct bond, methylene, O or S; m is 1, 2, 3, 4 or 5; provided that when m is 1, then X$^2$ is a direct bond; and R$^a$ and R$^b$ are independently hydrogen or (1–3C)alkyl or the group NR$^a$R$^b$ is pyrrolidino, piperidino, or morpholino; or $R^2$ is —X$^2$—(CH$_2$)$_n$—R$^f$ in which X$^2$ is a direct bond, methylene or O; n is 1, 2 or 3; and R$^f$ is 5-tetrazolyl, carboxy, [(1–4C)alkoxy]carbonyl or hydroxymethyl; and provided that at least one of $R^1$ and $R^2$ includes a basic amino moiety —NR$^s$R$^t$ or —NR$^a$R$^b$.

2. The compound (or salt thereof) of claim 1 wherein (1–3C)alkyl is methyl, ethyl, propyl or isopropyl; (1–4C)alkoxy is methoxy, ethoxy, propoxy, isopropoxy, butoxy or tert-butoxy; and halo is fluoro, chloro, bromo or iodo.

3. The compound (or pharmaceutically acceptable salt thereof) of formula I as claimed in claim 1 wherein $R^e$ is methyl, methoxy or bromo;
$R^1$ is —CO—NR$^s$R$^t$ or —X$^1$—(CH$_2$)$_s$—NR$^s$R$^t$; and
$R^2$ is —X$^2$—(CH$_2$)$_m$—NR$^a$R$^b$ or —X$^2$—(CH$_2$)$_n$—R$^f$ in which X$^2$ is O, n is 3, and R$^f$ is carboxy, [(1–4C)alkoxy]carbonyl or hydroxymethyl.

4. The compound (or pharmaceutically acceptable salt thereof) of formula I as claimed in claim 1, 2 or 3 wherein R$^e$ is methoxy;

R$^1$ is pyrrolidinocarbonyl or pyrrolidinomethyl; and

R$^2$ is 2-pyrrolidinoethoxy.

5. The compound (or pharmaceutically acceptable salt thereof) of formula I as claimed in claim 4 wherein R$^e$ is methoxy and R$^1$ is pyrrolidinomethyl.

6. The salt as claimed in claim 1 which is an acid-addition salt made with an acid which provides a pharmaceutically acceptable anion or, for a compound of formula I which bears an acidic moiety, which is the salt made with a base which affords a pharmaceutically acceptable cation.

7. A pharmaceutical formulation comprising in association with a pharmaceutically acceptable carrier, diluent or excipient, a compound of formula I (or a pharmaceutically acceptable salt thereof) as provided in claim 1.

8. A method of inhibiting thrombin comprising using an effective amount of a thrombin inhibiting compound of formula I (or a pharmaceutically acceptable salt thereof) as provided in claim 1.

9. A process for preparing a compound of formula I (or a pharmaceutically acceptable salt thereof) as claimed in claim 1 which comprises:

(a) Alkylating the 1-position of an azaindole of formula II

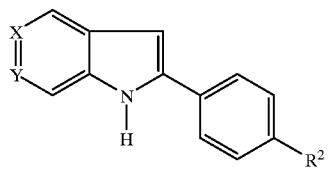

using a compound of formula III

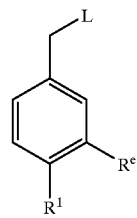

wherein L is a conventional leaving group;

(b) for a compound of formula I in which R$^1$ is —CO—NR$^s$R$^t$, amidating an ester of formula I in which R$^1$ is [(1–4C)alkoxy]carbonyl or an acid of formula I in which R$^1$ is carboxy or an activated derivative thereof with an amine of formula H—NR$^s$R$^t$; or (c) for a compound of formula I in which R$^1$ is —CH$_2$—NR$^s$R$^t$, reducing the carbonyl of a compound of formula I in which R$^1$ is —CO—NR$^s$R$^t$;

whereafter, for any of the above procedures, when a functional group is protected using a protecting group, removing the protecting group; and whereafter, for any of the above procedures, when a pharmaceutically acceptable salt of a compound of formula I is required, it is obtained by reacting the basic form of such a compound of formula I with an acid affording a physiologically acceptable counterion, or, for a compound of formula I which bears an acidic moiety, reacting the acidic form of such a compound of formula I with a base which affords a pharmaceutically acceptable cation, or by any other conventional procedure;

and wherein, unless otherwise described, X, Y, R$^1$, R$^2$ and R$^e$ have the values described in claim 1.

* * * * *